United States Patent
Woo et al.

(10) Patent No.: US 11,946,920 B2
(45) Date of Patent: Apr. 2, 2024

(54) HYDROGEN SENSOR HAVING VERTICAL NANOGAP STRUCTURE AND METHOD FOR MANUFACTURING THE SAME

(71) Applicant: KOREA INSTITUTE OF SCIENCE AND TECHNOLOGY, Seoul (KR)

(72) Inventors: Deok Ha Woo, Seoul (KR); Yusin Pak, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 433 days.

(21) Appl. No.: 17/148,242

(22) Filed: Jan. 13, 2021

(65) Prior Publication Data
US 2021/0239666 A1 Aug. 5, 2021

(30) Foreign Application Priority Data
Jan. 31, 2020 (KR) .................. 10-2020-0011940

(51) Int. Cl.
*G01N 33/00* (2006.01)
*H01L 21/02* (2006.01)

(52) U.S. Cl.
CPC ..... *G01N 33/005* (2013.01); *H01L 21/02107* (2013.01)

(58) Field of Classification Search
CPC .................................................. G01N 33/005
USPC ............................................ 73/31.05, 31.06
See application file for complete search history.

(56) References Cited

U.S. PATENT DOCUMENTS

| 8,211,586 B2 * | 7/2012 | Nakakubo ............... G01N 27/16 429/468 |
| 2005/0155858 A1 * | 7/2005 | Monty ................. G01N 33/005 204/431 |
| 2008/0038590 A1 * | 2/2008 | Nakakubo ............... G01N 27/16 429/468 |
| 2010/0108529 A1 * | 5/2010 | Zamborini ........... G01N 33/005 205/205 |
| 2013/0255358 A1 | 10/2013 | Lee et al. |
| 2016/0341688 A1 * | 11/2016 | Lim ................. G01N 33/48721 |

(Continued)

FOREIGN PATENT DOCUMENTS

| JP | 2008039658 A | 2/2008 |
| JP | 2011075421 A * | 4/2011 |
| KR | 10-0990815 B1 | 10/2010 |

(Continued)

OTHER PUBLICATIONS

Machine Translation of JP-2011075421-A (Year: 2011).*
(Continued)

*Primary Examiner* — Nathaniel J Kolb
(74) *Attorney, Agent, or Firm* — Rabin & Berdo, P.C.

(57) ABSTRACT

The present disclosure relates to a hydrogen sensor and a method for manufacturing the same, and more particularly, to a hydrogen sensor having a vertical nanogap structure, in which a nanogap is formed below a sensor portion to bring the sensor portion and an electrode into contact with each other when the sensor portion reacts with hydrogen, so as to allow the sensor portion to expand and contract freely without resistance on a substrate, thereby improving hydrogen sensing accuracy, and it is possible to form a precise nanogap with uniformity and reproducibility at a low cost and a method for manufacturing the same.

3 Claims, 6 Drawing Sheets

(56) References Cited

U.S. PATENT DOCUMENTS

2017/0336378 A1* 11/2017 Kim .................. G01N 33/0063
2020/0240942 A1* 7/2020 Prajapati .............. G01N 27/127

FOREIGN PATENT DOCUMENTS

| KR | 10-2013-0106032 A | 9/2013 |
| KR | 101431625 B1 | 8/2014 |
| KR | 10-1489154 B1 | 2/2015 |
| KR | 10-1775825 B1 | 9/2017 |
| KR | 101859851 B1 * | 5/2018 |
| KR | 1020180133734 A | 12/2018 |
| KR | 10-2110299 B1 | 5/2020 |

OTHER PUBLICATIONS

Machine Translation of KR-101859851 (Year: 2018).*
T Kiefer et al., "Large arrays of chemo-mechanical nanoswitches for ultralow-power hydrogen sensing", Journal of Micromechanics and Microengineering, 2010, pp. 1-9, vol. 20, No. 105019.

* cited by examiner

HYDROGEN SENSOR HAVING VERTICAL NANOGAP STRUCTURE AND METHOD FOR MANUFACTURING THE SAME

CROSS-REFERENCE TO RELATED APPLICATION

This application claims priority to Korean Patent Application No. 10-2020-0011940, filed on Jan. 31, 2020, and all the benefits accruing therefrom under 35 U.S.C. § 119, the contents of which in its entirety are herein incorporated by reference.

BACKGROUND

1. Field

The present disclosure relates to a hydrogen sensor and a method for manufacturing the same, and more particularly, to a hydrogen sensor having a vertical nanogap structure, in which a nanogap is formed below a sensor portion to bring the sensor portion and an electrode into contact with each other when the sensor portion reacts with hydrogen, so as to allow the sensor portion to expand and contract freely and rapidly without resistance on a substrate, thereby improving hydrogen sensing response and accuracy, and it is possible to form a precise nanogap with uniformity and reproducibility at a low cost and a method for manufacturing the same.

[Description about National Research and Development Support]

This study was supported by Support for vitalization of industry-academia-research cooperation Research and development program of Ministry of Science and ICT, Republic of Korea (Projects No. 1711102527) under the superintendence of Korea Institute for Advancement Technology.

2. Description of the Related Art

Hydrogen is widely used in different fields of industry including oil, chemicals and steel, and with the commercialization of hydrogen fuel cells, the use in daily life is increasing.

However, because hydrogen is flammable, when the concentration of hydrogen in air is 4% or greater, hydrogen burns by external stimuli such as heat, sparks and sunlight and thus caution is required. However, hydrogen is colorless, odorless and tasteless, and due to its unique properties, it is difficult to detect hydrogen leaking, and thus sensors for easily detecting leaking hydrogen as described in the following Patent Literature have been widely developed.

Figure 1:
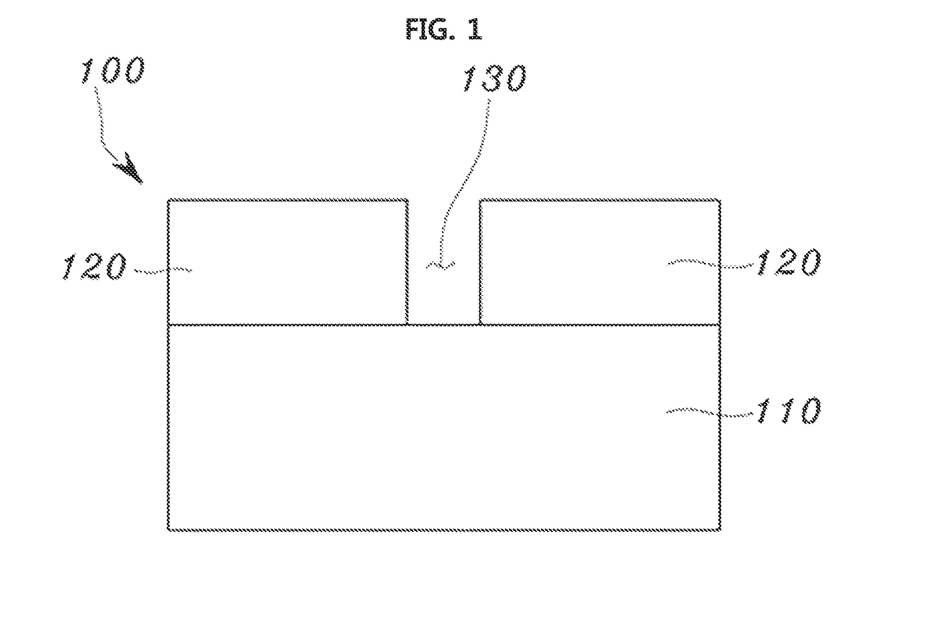
FIG. 1 is a front view of a hydrogen sensor according to the related art.

FIG. 1 is a front view of a typical hydrogen sensor according to the related art, and describing the structure and working principle of the hydrogen sensor according to the related art with reference to FIG. 1, the hydrogen sensor 100 includes a substrate 110, a pair of sensor portions 120 disposed on the substrate 110, spaced a predetermined distance apart from each other, a nanogap 130 formed by the separation of the pair of sensor portions 120, and an electrode (not shown) connected to the pair of sensor portions 120, wherein the pair of sensor portions 120 are made of transition metal (typically palladium) that expands in reaction with hydrogen, and in the absence of hydrogen, even though the current is supplied to the electrode, the current does not flow by the nanogap and an extremely high resistance or infinite resistance is measured, while in the presence of hydrogen, the pair of sensor portions expand and come into contact with each other, allowing the current to flow and resulting in a low resistance, and when hydrogen is removed, the pair of sensor portions contract and they are disconnected, so the current does not flow by the nanogap and a high resistance is measured, and accordingly it is possible to detect hydrogen by measuring a change in resistance.

However, in the hydrogen sensor 100 according to the related art, the sensor portion 120 expands and contracts in the horizontal direction according to the presence or absence of hydrogen, and in this instance, resistance occurs by the substrate 110, which restricts the deformation of the sensor portion 120, resulting in low accuracy of hydrogen sensing. On the other hand, a polymer layer (not shown) may be formed between the substrate 110 and the sensor portion 120 to reduce the interfacial resistance between the substrate 110 and the sensor portion 120, but in this case, it is necessary to separately form the polymer layer, which makes a fabrication process complicated. Additionally, a method for manufacturing the hydrogen sensor according to the related art is difficult to form the nanogap with uniformity and reproducibility at a low cost.

RELATED LITERATURES

Patent Literatures (Patent Literature 1) Korean Patent No. 10-1489154

SUMMARY

The present disclosure is designed to solve the above-described problem, and therefore the present disclosure is directed to providing a hydrogen sensor having a vertical nanogap structure, in which a nanogap is formed below a sensor portion to bring the sensor portion and an electrode into contact with each other when the sensor portion reacts with hydrogen, so as to allow the sensor portion to expand and contract freely without resistance on a substrate, thereby improving hydrogen sensing accuracy and a method for manufacturing the same.

The present disclosure is further directed to providing a hydrogen sensor having a vertical nanogap structure for manufacturing a precise nanogap with uniformity and reproducibility at a low cost and a method for manufacturing the same.

To achieve the above-described object, the present disclosure is embodied by the embodiment having the following configuration.

According to an embodiment of the present disclosure, a hydrogen sensor according to the present disclosure includes a substrate having an electrode, a sensor portion spaced a predetermined distance apart from an upper surface of the substrate, and a nanogap formed by vertical separation of the substrate and the sensor portion, wherein the sensor portion is made of a material that expands in reaction with hydrogen, and in the presence of hydrogen, the sensor portion expands and comes into contact with the underlying electrode.

According to another embodiment of the present disclosure, the hydrogen sensor according to the present disclosure may further include a support portion coupled to the upper surface of the substrate to support the sensor portion such that the sensor portion is spaced the predetermined distance apart from the substrate, the support portion being made of an insulating material.

According to another embodiment of the present disclosure, in the hydrogen sensor according to the present disclosure, the support portion may include a first support portion coupled to the upper surface of the substrate, and a second support portion coupled to the upper surface of the substrate, spaced a predetermined distance apart from the first support portion in a horizontal direction, and the sensor portion may include a seating portion seated on an upper surface of the support portion, and a protrusion protruding downwards from a lower surface of the seating portion and disposed between the first support portion and the second support portion.

According to another embodiment of the present disclosure, in the hydrogen sensor according to the present disclosure, the protrusion may be spaced a predetermined distance apart from the substrate in a vertical direction to form a nanogap between an end of the protrusion and the substrate, and may be spaced a predetermined distance apart from the support portion in a horizontal direction to prevent a contact with the support portion disposed on the outside of the protrusion during expansion of the protrusion.

According to another embodiment of the present disclosure, in the hydrogen sensor according to the present disclosure, the support portion may include a first support portion coupled to the upper surface of the substrate, and a second support portion coupled to the upper surface of the substrate, spaced a predetermined distance apart from the first support portion in a horizontal direction, and the sensor portion may include a top portion seated on an upper surface of the first support portion or the second support portion with an end disposed at an upper part between the first support portion and the second support portion, and a protrusion protruding from a lower surface of the top portion and disposed between the first support portion and the second support portion, spaced a predetermined distance apart from the substrate.

According to another embodiment of the present disclosure, in the hydrogen sensor according to the present disclosure, the protrusion may be spaced a predetermined distance apart from the substrate in a vertical direction to form the nanogap between an end of the protrusion and the substrate, and may be spaced a predetermined distance apart from the support portion in a horizontal direction to prevent a contact with the support portion disposed on the outside of the protrusion during expansion of the protrusion.

According to another embodiment of the present disclosure, a method for manufacturing a hydrogen sensor according to the present disclosure includes a first sacrificial layer formation step of forming a first sacrificial layer on a substrate having an electrode to a predetermined thickness, a support portion formation step of forming a support portion having insulating properties on the outside of the first sacrificial layer, spaced a predetermined distance apart from the first sacrificial layer after the first sacrificial layer formation step, a second sacrificial layer formation step of forming a second sacrificial layer having a spacer disposed between the first sacrificial layer and the support portion and a side protrusion protruding from a side of the spacer to a predetermined length and disposed at part of an upper surface of the first sacrificial layer after the support portion formation step, a sensor portion formation step of forming a sensor portion supported on the support portion with an end contacting the first sacrificial layer through deposition of a metal that expands in reaction with hydrogen after the second sacrificial layer formation step, and a nanogap formation step of forming a nanogap by removing the first sacrificial layer and the second sacrificial layer after the sensor portion formation step, wherein a thickness of the nanogap formed by the separation of the substrate and the sensor portion is adjusted by adjusting a thickness of the first sacrificial layer.

According to another embodiment of the present disclosure, a method for manufacturing a hydrogen sensor according to the present disclosure includes a first sacrificial layer formation step of forming a first sacrificial layer on a substrate having an electrode to a predetermined thickness, a support portion formation step of forming a support portion having insulating properties on the outside of the first sacrificial layer, spaced a predetermined distance apart from the first sacrificial layer after the first sacrificial layer formation step, a protrusion formation step of forming a protrusion on the first sacrificial layer to a predetermined thickness through deposition of a metal that expands in reaction with hydrogen after the support portion formation step, a second sacrificial layer formation step of forming a second sacrificial layer having a spacer disposed between the first sacrificial layer and the support portion and a side protrusion protruding from a side of the spacer to a predetermined length with a lower surface contacting an upper surface of the first sacrificial layer and a side contacting a side of the protrusion after the protrusion formation step, a seating portion formation step of forming a seating portion supported on the support portion and contacting the protrusion at a central area of a lower surface through deposition of a metal that expands in reaction with hydrogen after the second sacrificial layer formation step, and a nanogap formation step of forming a nanogap by removing the first sacrificial layer and the second sacrificial layer after the seating portion formation step, wherein a thickness of the nanogap formed by the separation of the substrate and the sensor portion is adjusted by adjusting a thickness of the first sacrificial layer.

According to another embodiment of the present disclosure, in the method for manufacturing a hydrogen sensor according to the present disclosure, the substrate may be made of a conductive material or may be an insulating substrate coated with a conductive material, the first sacrificial layer may be made of silicon dioxide, the support portion may be made of aluminum oxide, and the second sacrificial layer may be made of polyvinyl alcohol (PVA) that is dissolved in water.

The present disclosure can obtain the following effect by the combination and usage relationship between the above-described embodiments and the configuration described below.

The present disclosure forms the nanogap below the sensor portion to bring the sensor portion and the electrode into contact with each other when the sensor portion reacts with hydrogen, so as to allow the sensor portion to expand and contract freely without resistance on the substrate, thereby improving hydrogen sensing accuracy.

In addition, the present disclosure can manufacture a precise nanogap with uniformity and reproducibility at a low cost.

DETAILED DESCRIPTION

Hereinafter, exemplary embodiments of a hydrogen sensor having a vertical nanogap structure according to the present disclosure and a method for manufacturing the same will be described in detail with reference to the accompanying drawings. Note that like elements in the accompanying drawings are indicated by like reference signs anywhere in the specification as possible. Unless otherwise expressly defined herein, all the terms used herein are the same as the general meanings of the corresponding terms understood by those having ordinary skill in the technical field pertaining to the present disclosure and where there is a conflict between the meanings of the terms used herein and the commonly used ones, the terms are defined by the definition used herein. In the specification, "comprising" specifies the presence of stated elements, but does not preclude the presence or addition of other elements, unless the context clearly indicates otherwise. Additionally, in describing the present disclosure, when a certain description of known functions or elements is determined to make the subject matter of the present disclosure unnecessarily ambiguous, the detailed description will be omitted herein.

Figure 2:
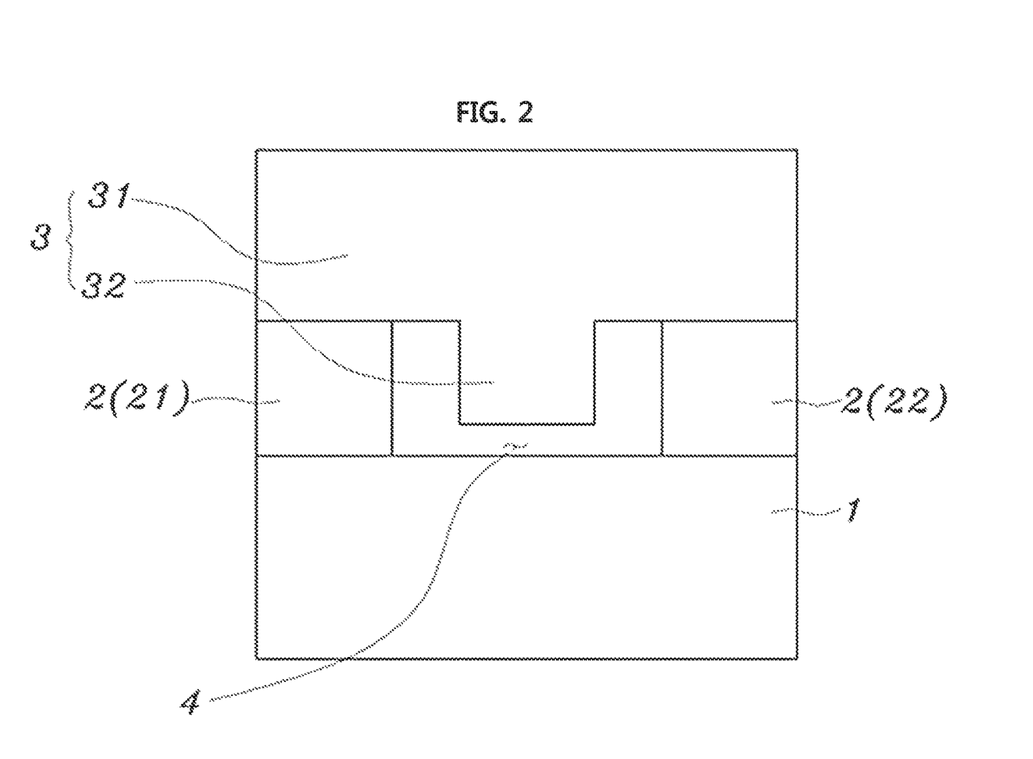
FIG. 2 is a front view of a hydrogen sensor according to an embodiment of the present disclosure.

Describing a hydrogen sensor having a vertical nanogap structure according to an embodiment of the present disclosure with reference to FIG. 2, the hydrogen sensor includes a substrate 1 having an electrode (not shown), a support portion 2 coupled to the upper surface of the substrate 1 to support a sensor portion 3 such that the sensor portion 3 is spaced a predetermined distance apart from the substrate 1, the sensor portion 3 disposed at the predetermined distance from the upper surface of the substrate 1 with the support of the support portion 2, and a nanogap 4 formed by the separation of the substrate 1 and the sensor portion 3, wherein the sensor portion 3 is made of a material that expands in reaction with hydrogen, and in the presence of hydrogen, the sensor portion 3 expands and comes into contact with the underlying electrode.

The substrate 1 forms the lower surface of the hydrogen sensor, and the substrate 1 may be made of a conductive material and perform the function of the electrode itself, or the substrate 1 may be made of a material having insulating properties, for example, polymer such as polydimethylsiloxane (PDMS), glass and silicon, and the electrode (not shown) may be formed on the upper surface of the substrate by coating. The electrode may be made of a material used to form the electrode in the hydrogen sensor according to the related art, and for example, a material having high conductivity such as silver, copper and gold.

The support portion 2 is coupled to the upper surface of the substrate 1 to support the sensor portion 3 such that the sensor portion 3 is spaced the predetermined distance apart from the substrate 1, and the support portion 2 may be made of a material having insulating properties, for example, aluminum oxide ($Al_2O_3$). The support portion 2 includes a first support portion 21 coupled to the upper surface of the substrate 1, and a second support portion 22 coupled to the upper surface of the substrate 1, spaced a predetermined distance apart from the first support portion 21 in the horizontal direction.

The sensor portion 3 is spaced the predetermined distance apart from the upper surface of the substrate 1 with the support of the support portion 2, and includes a seating portion 31 and a protrusion 32. The sensor portion 3 may be made of a material that expands in reaction with hydrogen, and for example, transition metal such as palladium (Pd).

The seating portion 31 is seated on the upper surface of the support portion 2, and the seating portion 31 has a predetermined shape, but may have a shape of a rectangular plate having a predetermined thickness.

The protrusion 32 protrudes in a downward direction from the lower surface of the seating portion 31, and is disposed between the first support portion 21 and the second support portion 22, spaced a predetermined distance apart from the substrate 1. The protrusion 32 is spaced the predetermined distance apart from the substrate 1 in the vertical direction to form the nanogap 4 between the end of the protrusion 32 and the substrate 1, and the protrusion 32 is spaced a predetermined distance apart from the support portion 2 in the horizontal direction to prevent the contact with the support portion 2 disposed on the outside of the protrusion 32 during expansion of the protrusion 32.

The nanogap 4 is formed by the separation of the substrate 1 and the sensor portion 3. Describing the hydrogen sensing process of the hydrogen sensor having the above-described configuration, in the absence of hydrogen, the sensor portion 3 does not react and thus there is no change in shape, but in the presence of hydrogen, the sensor portion 3 expands and the end of the protrusion 32 moves down and comes into contact with the electrode on the substrate 1, and subsequently, when hydrogen is removed, the sensor portion 3 contracts, the end of the protrusion 32 moves up away from the electrode on the substrate 1. Each of the sensor portion 3 and the electrode is connected to a wiring in which the current flows, and in the above-described process, when the sensor portion 3 does not come into contact with the electrode, the current does not flow and a large resistance value is measured, but when the sensor portion 3 comes into contact with the electrode, the current flows and a small resistance value is measured, so it is possible to sense hydrogen by detecting a change in the resistance value. As opposed to the related art, the present disclosure forms a nanogap of a vertical structure to allow the sensor portion to expand downwards without resistance, thereby increasing hydrogen sensing accuracy.

Figure 3:
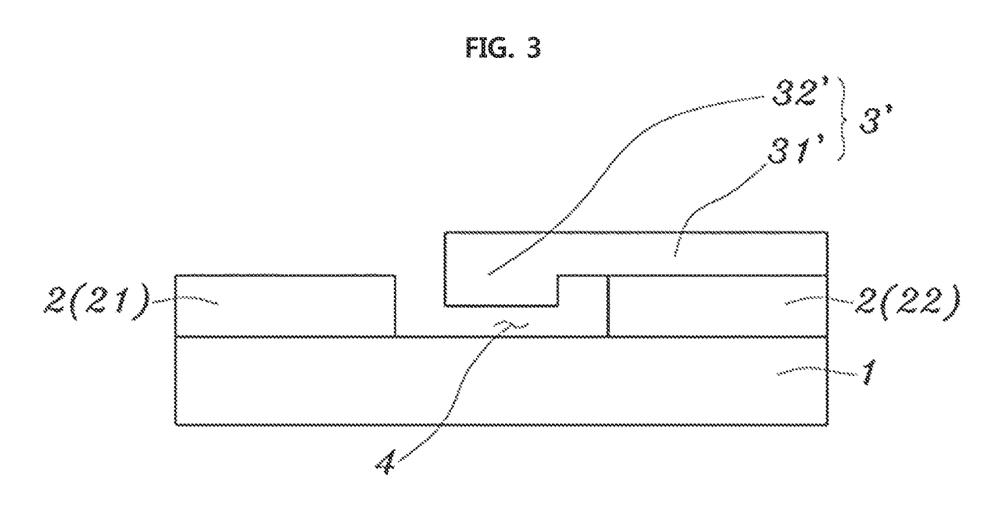
FIG. 3 is a front view of a hydrogen sensor according to another embodiment of the present disclosure.

Describing a hydrogen sensor having a vertical nanogap structure according to another embodiment of the present disclosure with reference to FIG. 3, the hydrogen sensor includes a substrate 1, a support portion 2, a sensor portion 3' and a nanogap 4, and except the shape of the sensor portion 3', each of the substrate 1, the support portion 2 and the nanogap 4 has the same shape as the substrate 1, the support portion 2 and the nanogap 4 described with reference to FIG. 2, and only the sensor portion 3' will be described below.

The sensor portion 3' is spaced a predetermined distance apart from the upper surface of the substrate 1 with the support of the support portion 2, and includes a top portion 31' seated on the upper surface of a first support portion 21 or a second support portion 22 with the end disposed at the upper part between the first support portion 21 and the second support portion 22, and a protrusion 32' protruding from the lower surface of the top portion 31' and disposed between the first support portion 21 and the second support portion 22, spaced a predetermined distance apart from the substrate 1. The sensor portion 3' has a predetermined shape but may have an "L" shape. The protrusion 32' is spaced the predetermined distance apart from the substrate 1 in the vertical direction to form the nanogap 4 between the end of the protrusion 32' and the substrate 1, and the protrusion 32' is spaced a predetermined distance apart from the support portion 2 in the horizontal direction to prevent the contact with the support portion 2 disposed on the outside of the protrusion 32' during expansion of the protrusion 32'.

Describing the hydrogen sensing process of the hydrogen sensor having the above-described configuration, in the absence of hydrogen, the sensor portion 3' does not react and thus there is no change in shape, but in the presence of hydrogen, the sensor portion 3' expands and the end of the protrusion 32' moves down and comes into contact with the electrode on the substrate 1, and subsequently, when hydrogen is removed, the sensor portion 3' contracts and the end of the protrusion 32' moves up away from the electrode on the substrate 1. Each of the sensor portion 3' and the electrode is connected to a wiring in which the current flows, and in the above-described process, when the sensor portion 3' does not come into contact with the electrode, the current does not flow and a large resistance value is measured, but when the sensor portion 3' comes into contact with the electrode, the current flows and a small resistance value is measured, so it is possible to sense hydrogen by detecting a change in the resistance value. That is, the hydrogen sensor works in atomic force microscopy (AFM) tip-like contact mode.

Describing a method for manufacturing the hydrogen sensor having a vertical nanogap structure described with reference to FIG. 2 with reference to FIGS. 2, 4 and 5, the method for manufacturing the hydrogen sensor includes a first sacrificial layer formation step of forming a first sacrificial layer 5 on a substrate 1 having an electrode (not shown) to a predetermined thickness, a support portion formation step of forming a support portion 2 having insulating properties on the outside of the first sacrificial layer 5, spaced a predetermined distance apart from the first sacrificial layer 5 after the first sacrificial layer formation step, a second sacrificial layer formation step of forming a second sacrificial layer 6 having a spacer 61 disposed the first sacrificial layer 5 and the support portion 2 and a side protrusion 62 protruding from the side of the spacer 61 to a predetermined length and disposed at part of the upper surface of the first sacrificial layer 5 after the support portion formation step, a sensor portion formation step of forming a sensor portion 3 supported on the support portion 2 with the end contacting the first sacrificial layer 5 through deposition of a metal that expands in reaction with hydrogen after the second sacrificial layer formation step, and a nanogap formation step of forming a nanogap 4 by removing the first sacrificial layer 5 and the second sacrificial layer 6 after the sensor portion formation step, wherein the nanogap formed by the separation of the substrate 1 and the sensor portion 3 may be formed precisely and easily by adjusting the thickness of the first sacrificial layer 5.

Figure 4A:
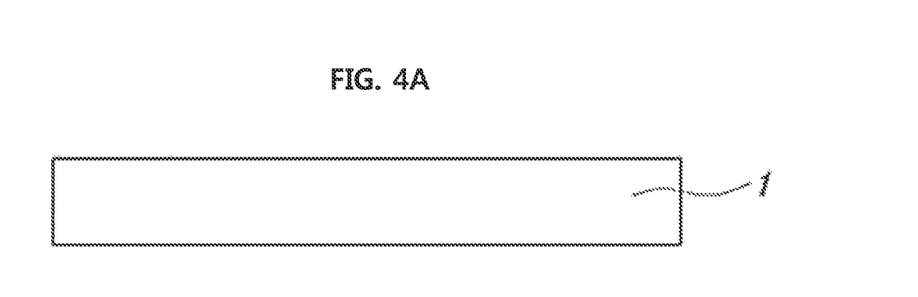
FIG. 4A to FIG. 4C, FIG. 5A to FIG. 5C and FIG. 6A to FIG. 6D are reference views for describing a process of manufacturing the hydrogen sensor of FIG. 2.
Figure 4B:
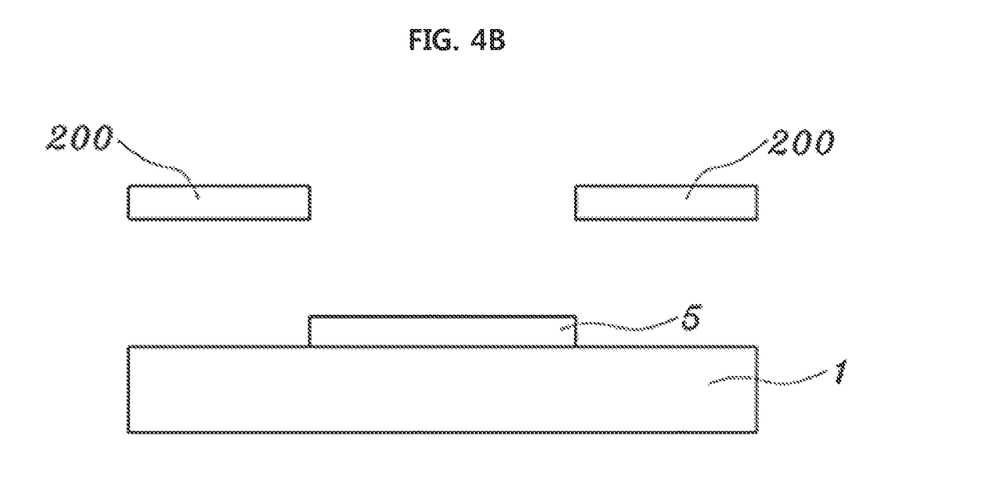
Figure 4C:
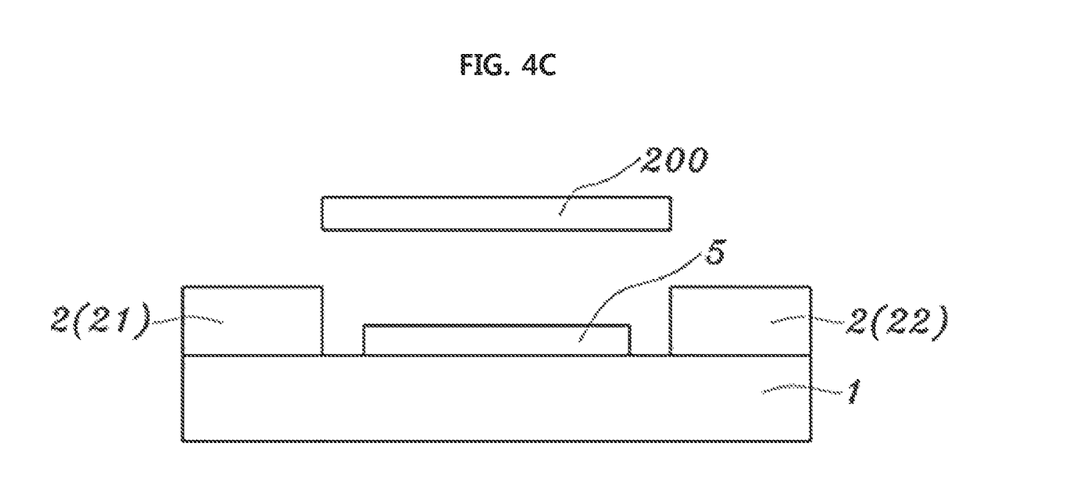

The first sacrificial layer formation step is the step of forming the first sacrificial layer 5 on the substrate 1 having the electrode (not shown) to a predetermined thickness, and for example, the first sacrificial layer 5 may be formed at the central area of the upper surface of the substrate 1 to a predetermined thickness as shown in (B) of FIG. 4A to FIG. 4C through deposition of a material that can be removed by etching on the upper surface of the substrate 1 having the electrode (not shown) as shown in FIG. 4A using a metal shadow mask 200 disposed at a predetermined distance. The substrate 1 may be made of a conductive material or may be an insulating substrate coated with a conductive material, and the first sacrificial layer 5 may be made of silicon dioxide ($SiO_2$) and formed by a deposition method, for example, plasma enhanced chemical vapor deposition (PECVD) and electron beam (E-beam) evaporation.

The support portion formation step is the step of forming the support portion 2 having insulating properties on the outside of the first sacrificial layer 5, spaced a predetermined distance apart from the first sacrificial layer 5 after the first sacrificial layer formation step, and for example, a first support portion 21 and a second support portion 22 spaced a predetermined distance apart from each other in the horizontal direction may be formed on the upper surface of the substrate 1 through deposition of a material having insulating properties using the metal shadow mask 200 disposed above the first sacrificial layer 5 as shown in FIG. 4C. The support portion 2 may be made of, for example, aluminum oxide ($Al_2O_3$).

Figure 5A:
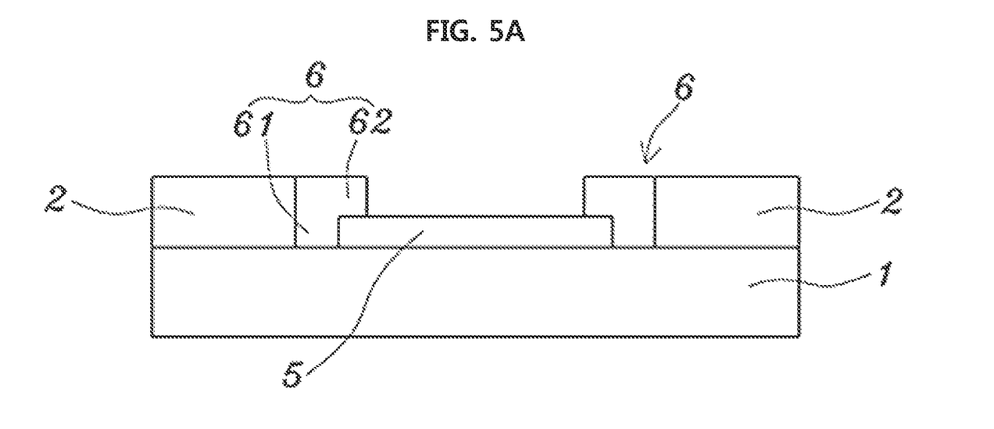

The second sacrificial layer formation step is the step of forming the second sacrificial layer 6 having the spacer 61 disposed between the first sacrificial layer 5 and the support portion 2 and the side protrusion 62 protruding from the side of the spacer 61 to a predetermined length and disposed at part of the upper surface of the first sacrificial layer 5 after the support portion formation step, and for example, a pair of second sacrificial layers 6 spaced a predetermined distance apart from each other in the horizontal direction may be formed on the upper surface of the substrate 1 using a photolithography process as shown in FIG. 5A. The second sacrificial layer 6 may be made of, for example, PVA that is dissolved in water.

Figure 5B:
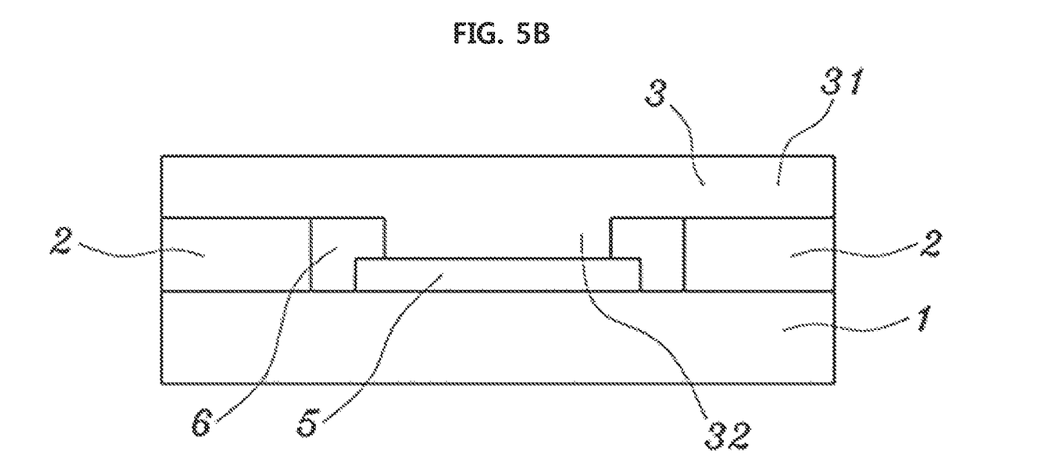

The sensor portion formation step is the step of forming the sensor portion 3 supported on the support portion 2 with the end contacting the first sacrificial layer 5 through deposition of a metal that expands in reaction with hydrogen after the second sacrificial layer formation step, and for example, as shown in FIG. 5B, the sensor portion 3 having a seating portion 31 supported on the support portion 2, and a protrusion 32 protruding from the central area of the lower surface of the seating portion 31 with the lower surface contacting the first sacrificial layer 5 and the side contacting the second sacrificial layer 6 may be formed through deposition of a metal that expands in reaction with hydrogen on the upper surface of the support portion 2, the first sacrificial layer 5 and the second sacrificial layer 6. The sensor portion may be made of palladium that expands in reaction with hydrogen.

Figure 5C:
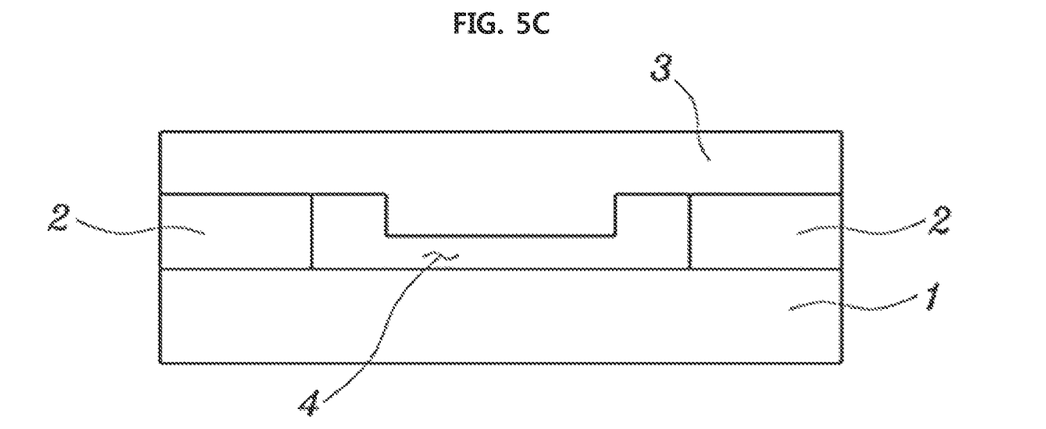

In the nanogap formation step, after the sensor portion formation step, the nanogap 4 is formed by removing the first sacrificial layer 5 and the second sacrificial layer 6, and for example, the nanogap 4 may be formed by dissolving the second sacrificial layer 6 in water and removing the first sacrificial layer 5 through the existing etching method so that the substrate 1 and the sensor portion 3 are spaced apart from each other as shown in FIG. 5C. In the present disclosure, the nanogap 4 has the same size as the thickness of the first sacrificial layer 5, and thus the nanogap formed by the separation of the substrate 1 and the sensor portion 3 may be formed precisely and easily by adjusting the thickness of the first sacrificial layer 5.

Describing another method for manufacturing the hydrogen sensor having a vertical nanogap structure described with reference to FIG. 2 with reference to FIGS. 2, 4 and 6, the method for manufacturing the hydrogen sensor includes a first sacrificial layer formation step, a support portion formation step, a protrusion formation step, a second sacrificial layer formation step, a seating portion formation step and a nanogap formation step, and each of the first sacrificial layer formation step, the support portion formation step and the nanogap formation step is the same as the first sacrificial layer formation step, the support portion formation step and the nanogap formation step of the method for manufacturing the hydrogen sensor described previously with reference to 2, 4 and 5, and only the protrusion formation step, the second sacrificial layer formation step and the seating portion formation step will be described below.

Figure 6A:
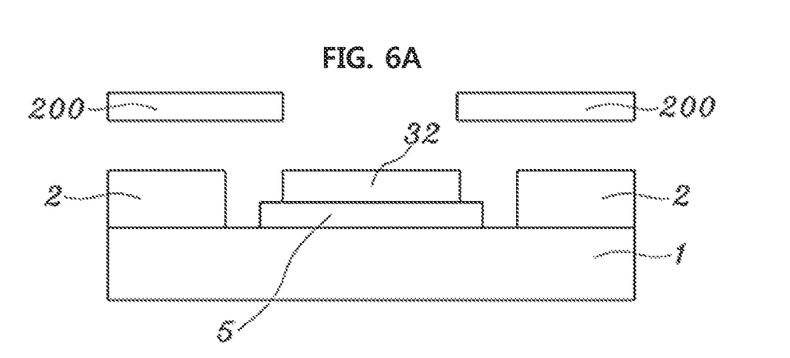

The protrusion formation step is the step of forming the protrusion 32 on the first sacrificial layer 5 to a predetermined thickness through deposition of a metal that expands in reaction with hydrogen after the support portion formation step, and for example, the protrusion 32 may be formed at the central area of the upper surface of the first sacrificial layer 5 to a predetermined thickness through deposition of a metal that expands in reaction with hydrogen on the upper surface of the first sacrificial layer 5 using the metal shadow mask 200 disposed at a predetermined distance as shown in FIG. 6A. The protrusion 32 may have a horizontal width that is smaller than a horizontal width of the first sacrificial layer 5.

Figure 6B:
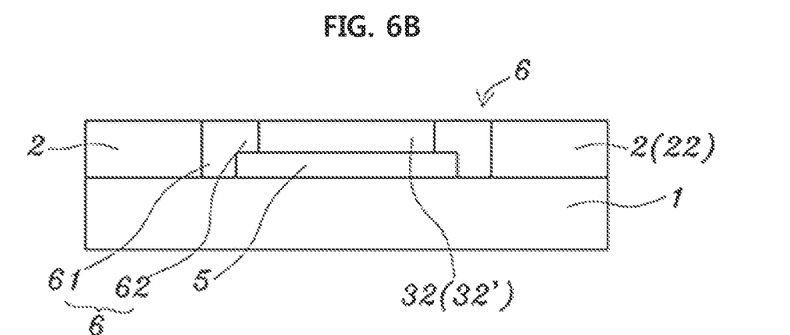

The second sacrificial layer formation step is the step of forming the second sacrificial layer 6 having the spacer 61 disposed between the first sacrificial layer 5 and the support portion 2 and the side protrusion 62 from the side of the spacer 61 to a predetermined length with the lower surface contacting the upper surface of the first sacrificial layer 5 and the side contacting the side of the protrusion 32 after the protrusion formation step, and for example, a pair of second sacrificial layers 6 spaced a predetermined distance apart from each other in the horizontal direction may be formed on the upper surface of the substrate 1 using PVA dipping, followed by spin coating, baking and reactive ion etching oxygen (O 2) plasma for exposure of the upper surface of the protrusion 32, or a gap filling solution used in a semiconductor process, as shown in FIG. 6B. The second sacrificial layer 6 may be made of, for example, PVA that is dissolved in water.

Figure 6C:
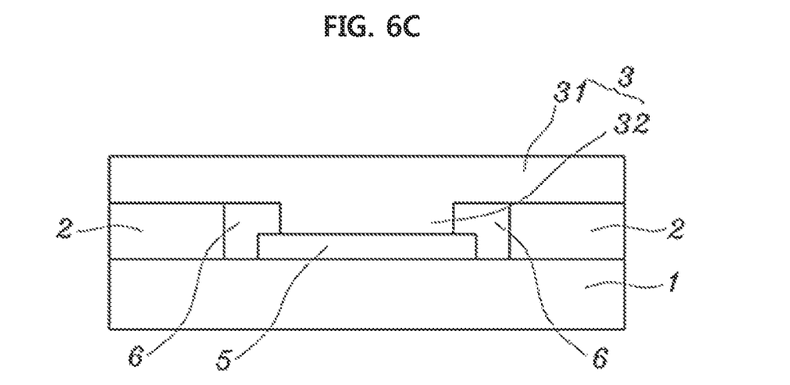
Figure 6D:
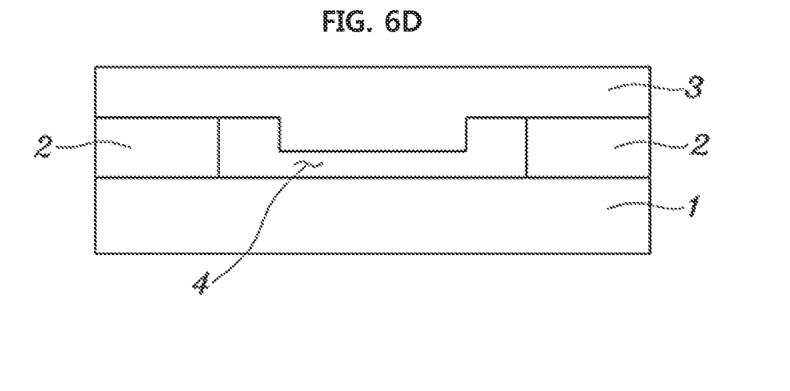

The seating portion formation step is the step of forming the seating portion 31 supported on the support portion 2 and contacting the protrusion 32 at the central area of the lower surface through deposition of a metal that expands in reaction with hydrogen after the second sacrificial layer formation step, and for example, as shown in FIG. 6C, the seating portion 31 supported on the support portion 2 and contacting the protrusion 32 at the central area of the lower surface may be formed through deposition of a metal that expands in reaction with hydrogen on the upper surface of the support portion 2, the protrusion 31 and the second sacrificial layer 6 formed at the same level as shown in FIG. 6B. The seating portion 31 is made of the same material as the material of the protrusion 32. After the seating portion formation step, the nanogap 4 may be formed by dissolving the second sacrificial layer 6 in water and removing the first sacrificial layer 5 through the existing etching method so that the substrate 1 and the sensor portion 3 are spaced apart from each other as shown in FIG. 6D. As opposed to the above-described manufacturing method, another method for manufacturing the hydrogen sensor is performed using a shadow mask based direct deposition process without using the photolithography method.

Describing a method for manufacturing the hydrogen sensor having a vertical nanogap structure described with reference to FIG. 3 with reference to FIGS. 3, 4, 6 and 7, the method for manufacturing the hydrogen sensor includes a first sacrificial layer formation step, a support portion formation step, a protrusion formation step, a second sacrificial layer formation step, a top portion formation step and a nanogap formation step, and each of the first sacrificial layer formation step, the support portion formation step, the protrusion formation step, the second sacrificial layer formation step and the nanogap formation step is the same as the first sacrificial layer formation step, the support portion formation step, the protrusion formation step, the second sacrificial layer formation step and the nanogap formation step of another method for manufacturing the hydrogen sensor described previously with reference to FIGS. 2, 4 and 6, and only the top portion formation step will be described below.

Figure 7A:
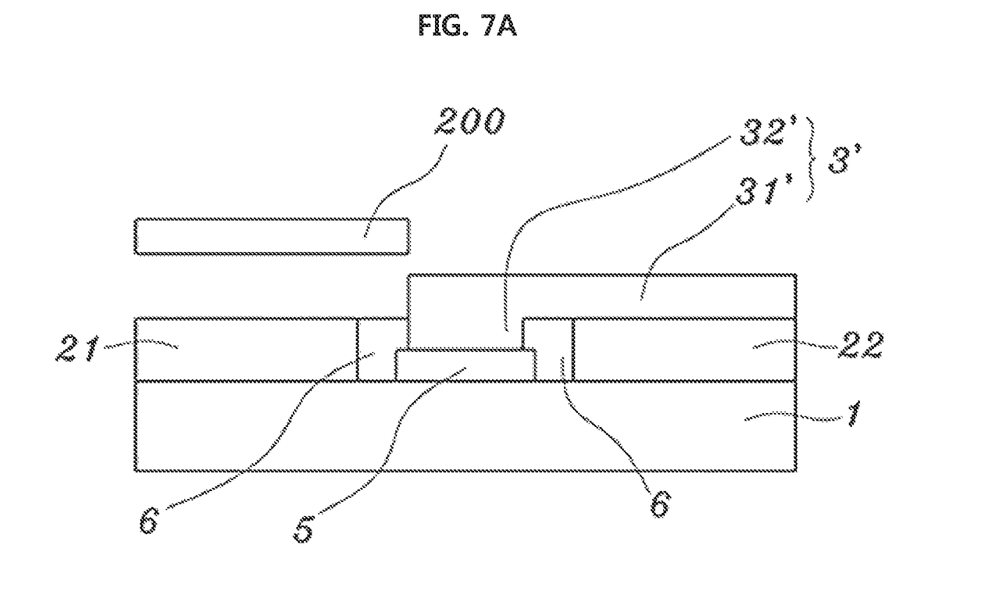
FIG. 7A and FIG. 7B are reference views for describing a process of manufacturing the hydrogen sensor of FIG. 3.
Figure 7B:
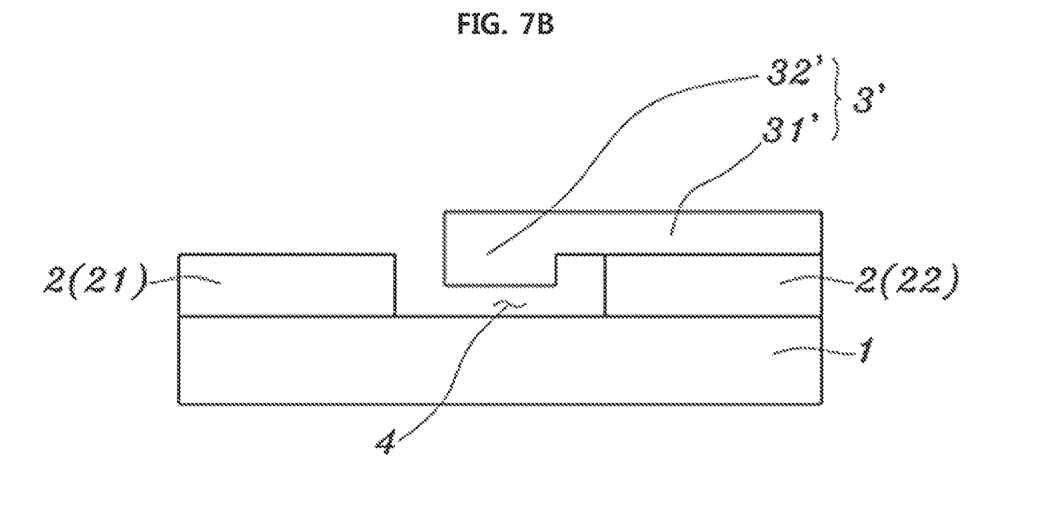

The top portion formation step is the step of forming the top portion 31' seated on the first support portion 21 or the second support portion 22 and contacting the protrusion 32' at the end of the lower surface through deposition of a metal that expands in reaction with hydrogen after the second sacrificial layer formation step, and for example, as shown in FIG. 7A, the top portion 31' seated on the second support portion 22 and contacting the protrusion 32' at the end of the lower surface may be formed through deposition of a metal that expands in reaction with hydrogen on the upper surface of the protrusion 32', the second sacrificial layer 6 and the second support portion 22 formed at the same level as shown in FIG. 6B using the metal shadow mask 200. After the top portion formation step, the nanogap 4 may be formed by dissolving the second sacrificial layer 6 in water and removing the first sacrificial layer 5 through the existing etching method so that the substrate 1 and the sensor portion 3' are spaced apart from each other as shown in FIG. 7B.

While various embodiments of the present disclosure have been hereinabove described, these embodiments are just an embodiment that realizes the technical spirit of the present disclosure, and it should be interpreted that any modification or variation that realizes the technical spirit of the present disclosure fall in the scope of the present disclosure.

[Detailed Description of Main Elements]

| | |
|---|---|
| 1: Substrate | 2: Support portion |
| 3, 3': Sensor portion | 4: Nanogap |
| 5: First sacrificial layer | 3: Second sacrificial layer |
| 21: First support portion | 22: Second support portion |
| 31: Seating portion | 32, 32': Protrusion |
| 61: Spacer | 62: Side protrusion |
| 31': Top portion | 100: Hydrogen sensor |
| 110: Substrate | 120: Sensor portion |
| 130: Nanogap | 200: Metal shadow mask |

What is claimed is:

1. A method for manufacturing a hydrogen sensor, comprising:
a first sacrificial layer formation step of forming a first sacrificial layer to a predetermined thickness on a substrate, the substrate being configured to perform a function of an electrode, a support portion formation step of forming a support portion having insulating properties on an outside of the first sacrificial layer, the support portion including a first support portion and a second support portion respectively spaced a predetermined distance apart from the first sacrificial layer after the first sacrificial layer formation step, a second sacrificial layer formation step of forming a second sacrificial layer having a spacer disposed between the first sacrificial layer and the support portion and a side protrusion protruding from a side of the spacer to a predetermined length and disposed at part of an upper surface of the first sacrificial layer after the support portion formation step, a sensor portion formation step of forming a sensor portion supported on the support portion with an end contacting the first sacrificial layer through deposition of a metal that expands in reaction with hydrogen after the second sacrificial layer formation step, and a nanogap formation step of forming a nanogap by removing the first sacrificial layer and the second sacrificial layer after the sensor portion formation step, wherein a thickness of the nanogap formed by the separation of the substrate and the sensor portion is adjusted by adjusting a thickness of the first sacrificial layer;

wherein the removing the first sacrificial layer and the second sacrificial layer after the seating portion formation step forms the nanogap to be bounded on opposing sides by the first support portion and the second support portion.

2. A method for manufacturing a hydrogen sensor, comprising:

a first sacrificial layer formation step of forming a first sacrificial layer to a predetermined thickness on a substrate, the substrate being configured to perform a function of an electrode, a support portion formation step of forming a support portion having insulating properties on an outside of the first sacrificial layer, the support portion including a first support portion and a second support portion respectively spaced a predetermined distance apart from the first sacrificial layer after the first sacrificial layer formation step, a protrusion formation step of forming a protrusion on the first sacrificial layer to a predetermined thickness through deposition of a metal that expands in reaction with hydrogen after the support portion formation step, a second sacrificial layer formation step of forming a second sacrificial layer having a spacer disposed between the first sacrificial layer and the support portion and a side protrusion protruding from a side of the spacer to a predetermined length with a lower surface contacting an upper surface of the first sacrificial layer and a side contacting a side of the protrusion after the protrusion formation step, a seating portion formation step of forming a seating portion supported on the support portion and contacting the protrusion at a central area of a lower surface through deposition of a metal that expands in reaction with hydrogen after the second sacrificial layer formation step, and a nanogap formation step of forming a nanogap by removing the first sacrificial layer and the second sacrificial layer after the seating portion formation step, wherein a thickness of the nanogap formed by the separation of the substrate and the sensor portion is adjusted by adjusting a thickness of the first sacrificial layer, and wherein the removing the first sacrificial layer and the second sacrificial layer after the seating portion formation step forms the nanogap to be bounded on opposing sides by the first support portion and the second support portion.

3. The method for manufacturing a hydrogen sensor according to claim 1, wherein the substrate is made of a conductive material or is an insulating substrate coated with a conductive material, the first sacrificial layer is made of silicon dioxide ($SiO_2$), the support portion is made of aluminum oxide ($Al_2O_3$), and the second sacrificial layer is made of polyvinyl alcohol (PVA) that is dissolved in water.

\* \* \* \* \*